(12) United States Patent
Crozet et al.

(10) Patent No.: US 6,217,578 B1
(45) Date of Patent: Apr. 17, 2001

(54) SPINAL CROSS CONNECTOR

(75) Inventors: Yves Crozet, Ramsey; Martin Masson, Newark, both of NJ (US)

(73) Assignee: Stryker Spine S.A. (FR)

( * ) Notice: Subject to any disclaimer, the term of this patent is extended or adjusted under 35 U.S.C. 154(b) by 0 days.

(21) Appl. No.: 09/419,869

(22) Filed: Oct. 19, 1999

(51) Int. Cl.$^7$ ................................................ A61B 17/70
(52) U.S. Cl. ............................................... 606/61; 606/60
(58) Field of Search ................... 606/60, 61, 69

(56) References Cited

U.S. PATENT DOCUMENTS

| | | | |
|---|---|---|---|
| 4,085,744 | 4/1978 | Lewis et al. | 128/69 |
| 4,257,409 | 3/1981 | Bacal et al. | 128/69 |
| 4,361,141 * | 11/1982 | Tanner | 60/60 |
| 4,404,967 * | 9/1983 | Bacal et al. | 606/61 |
| 4,567,884 | 2/1986 | Edwards | 128/69 |
| 4,716,894 | 1/1988 | Lazzeri et al. | 128/92 |
| 4,773,402 | 9/1988 | Asher et al. | 128/69 |
| 5,102,412 | 4/1992 | Rogozinski | 606/61 |
| 5,147,360 | 9/1992 | Dubousset | 606/61 |
| 5,154,718 | 10/1992 | Cozad et al. | 606/61 |
| 5,261,907 | 11/1993 | Vignaud et al. | 606/60 |
| 5,368,594 | 11/1994 | Martin et al. | 606/61 |
| 5,374,267 | 12/1994 | Siegal | 606/61 |
| 5,439,463 | 8/1995 | Lin | 606/61 |
| 5,443,465 | 8/1995 | Pennig | 606/59 |
| 5,454,812 * | 10/1995 | Lin | 606/61 |
| 5,522,816 * | 6/1996 | Dinello et al. | 606/61 |
| 5,601,552 | 2/1997 | Cotrel | 606/61 |
| 5,620,444 | 4/1997 | Assaker | 606/61 |
| 5,624,442 | 4/1997 | Mellinger et al. | 606/61 |
| 5,651,789 | 7/1997 | Cotrel | 606/61 |
| 5,667,507 | 9/1997 | Corin et al. | 606/61 |
| 5,702,393 | 12/1997 | Pfaifer | 606/61 |
| 5,709,684 * | 1/1998 | Errico et al. | 606/61 |
| 5,716,355 | 2/1998 | Jackson et al. | 606/61 |
| 5,743,911 | 4/1998 | Cotrel | 606/61 |
| 5,752,955 | 5/1998 | Errico | 606/61 |
| 5,800,548 | 9/1998 | Martin et al. | 623/17 |
| 5,827,283 | 10/1998 | Groiso et al. | 606/57 |
| 5,899,903 | 5/1999 | Cotrel | 606/61 |
| 5,947,966 | 9/1999 | Drewry et al. | 606/61 |
| 5,980,523 * | 11/1999 | Jackson | 606/61 |
| 6,077,263 * | 6/2000 | Ameil et al. | 606/61 |
| 6,083,226 * | 7/2000 | Fiz | 606/61 |
| 6,096,039 * | 8/2000 | Stoltenberg et al. | 606/61 |
| 6,113,600 * | 9/2000 | Drummond et al. | 606/61 |

FOREIGN PATENT DOCUMENTS

| | | | |
|---|---|---|---|
| 3807335 * | 9/1989 | (DE) | 606/61 |
| 0328883 * | 1/1989 | (EP) | 606/61 |
| 0461374 * | 4/1991 | (EP) | 606/61 |
| 0 446 092 B1 | 7/1995 | (EP) . | |
| 2645427 * | 4/1989 | (FR) | 606/61 |
| 2 645 427 | 10/1990 | (FR) . | |
| 2 659 223 | 9/1991 | (FR) . | |
| 2-215455 * | 2/1993 | (JP) | 606/61 |
| 2701833 * | 2/1993 | (FR) | 606/61 |

* cited by examiner

Primary Examiner—Gene Mancene
Assistant Examiner—Michael B. Priddy
(74) Attorney, Agent, or Firm—Lerner, David, Littenberg, Krumholz & Mentlik, LLP (57) ABSTRACT

A spinal cross connector connects a pair of longitudinally extending rods anchored to the spine. The cross connector has a first element, including a body, a rod gripping portion formed on a first end of the body and a circular arm extending along a first axis from a second end of the body. A second element is provided which has a body, a rod gripping portion formed on one end and a flange having a bore on a second end. The flange has a bearing surface surrounding the bore and another bearing surface it formed on the inner surface of the bore. A pivot element has a head portion, including a bore therethrough for engaging the arm on the first element. The pivot element has a threaded portion extending from the head along a second axis and a generally cylindrical bearing surface engageable with the bearing surface inside the bore. A lock nut is operatively engageable with the threaded portion on the pivot element to lock the assembly together.

48 Claims, 8 Drawing Sheets

SPINAL CROSS CONNECTOR

BACKGROUND OF THE INVENTION

1. Field of the Invention

The present invention relates to a vertebral osteosynthesis device that can be used to brace a spine, for example, following accidental fracture, or to strengthen or brace a deviated spine, as in the case scoliosis or kyphosis. More particularly, this invention is related to a novel cross connector which fixes the location and enhances the rigidity of longitudinally extending rods anchored to the spine.

2. Discussion of the Prior Art

As is known, from, for example, U.S. Pat. No. 5,055,562 to Cotrel, a pair of posterior rods may be coupled to the back of a spinal column by hooks held by screws supported by the pedicles of the vertebra. Generally, there are two rigid and substantially parallel support rods disposed one on each side of the spine supported by pedicle screws or hooks. These vertically aligned rods stabilize both short and long segments of the spine. Implantation of such a device requires the rods to be shaped to adapt to the curve in one or two planes of the spine, whether these are nature curves or curves resulting from scoliosis or kyphosis.

In order to provide enhanced rigidity, especially torsional rigidity, the pair of rods usually includes cross connecting devices which couple the rods together transverse to their longitudinal axis, i.e. transverse to an axis extending in the vertical direction when an individual is standing.

As can be seen from U.S. Pat. No. 5,005,562 these cross connector devices include a plurality hook shaped gripping elements which receive the rod. These elements are fixed to the rods by set screws which extend through a wall of the hook. Since the rods may be curved in the medial-lateral direction and the distance between the pair of rods may vary consequently, a method for varying the horizontal distance between the hooks is required. As can be seen in U.S. Pat. No. 5,002,562, one solution is to provide a threaded transverse rod on which the hooks may be threaded for movement therealong. Of course, this limits the adjustibility of the hooks, depending on the fineness of the thread and the required angular orientation necessary to engage the vertical rods.

Consequently, Cotrel, in his later U.S. Pat. Nos. 5,601,552 and 5,651,789 uses a transverse bar of polygonal shape which allows the hooks to slide and be fixed in any relative horizontal position along the bar. However, such a system exhibits only one degree of freedom since the hook surfaces always move in the same plane.

In U.S. Pat. No. 5,667,507 to Corin, et al., a cross locking member is provided, which includes an additional degree of freedom, allowing rotation in the vertical plane as well as length adjustment in the horizontal direction. Thus, two degrees of freedom are provided. Similarly, U.S. Pat. No. 5,752,955 provides two degrees of freedom by allowing rotation around a horizontally extending axis as well as allowing equalized extension via a telescoping connection between the hook bodies.

U.S. Pat. No. 5,443,465 to Pennig discloses a fracture fixation device having multiple degrees of freedom. However, this device requires several joints which have to be independently locked to fix the device in a given position.

U.S. Pat. No. 5,716,355 to Jackson, et al. relates to a pair of connectors slideable along each to two parallel spinal rods and having swivel connections to fix the final orientation of a transverse rod relative to the spinal rod. This design requires both connectors to be independently adjusted and locked to fix the transverse rod in its final position.

U.S. Pat. No. 5,261,907 to Vignaud, et al. relates to a cross connecting device having a pair of rods and a pair of clamps which can be fixed in place, utilizing a screw arrangements. This device is difficult to assemble because it includes two clamps, each receiving its own extension arm which arms are independently adjustable within the clamps.

None of the prior art discloses transverse cross connector having multiple degrees of freedom which cross connector can be locked in a desired position by a single locking mechanism.

SUMMARY OF THE INVENTION

It is therefore an object of the present invention to provide a cross connector device having a low profile but allowing for a substantial degree of freedom between the hooks at either end of the device.

It is also an object of the present invention to provide a cross connector device which, while providing multiple degrees of freedom, provides a surgeon with the ability to lock the device on a spinal rod with a set screw in a given orientation with a single locking mechanism, using only two tools, one for the locking mechanism and one for the set screw.

These and other objects of the invention are achieved by the present invention, which is a locking variable cross connector device which may be affixed to the rods of a dual rod spinal implant apparatus. This cross connector device includes a pair of rod engaging elements in the form of hooks.

The cross connector or link for connecting spinal rods of the present invention includes a first rod gripping element which, in the preferred embodiment, is in the form of a hook formed on a first end of the rod gripping element and including an arm or rod extending from a second end thereof along a first axis. A second rod gripping element is provided which also includes hook formed on a first end thereof and a bearing portion with a bearing surface surrounding a bore or hole integrally formed on a second end thereof. A pivot element is slidably and rotatably coupled to the arm on the first rod gripping element, via a bore in the pivot element for movement therealong and for rotation about the first axis. The pivot element includes a bearing surface engageable with the bearing surface formed on the second element. These bearing surfaces allow relative rotation between the pivot element and the second rod gripping element about a second axis which is not parallel to the first axis.

In the preferred embodiment, the second axis is perpendicular to the first axis to allow relative angular adjustment between the two hook portions in the vertical plane of the spine. As used herein, the vertical plane refers to the plane through the spine in the medial lateral direction which is parallel to the front or coronal plane.

The pivot element has a first clamping portion associated with the bore therein which engages the arm and a second clamping portion in the form of a lock nut which engages the bearing member on the second rod gripping element. The clamping portions of the pivot element are designed to clamp the arm and a bearing surface on the second rod gripping element to prevent all rotation about the first and second axis and all movement along the arm. This may be accomplished by the frictional engagement between a bearing surface on the second element while clamped between the lock nut, and the surface of the arm and the engagement of the first clamping portion in the bore of the pivot element contacting the opposite side of the arm.

In the preferred embodiment, the arm on the first bearing element may be in the form of a longitudinally extending rod or shaft having a circular cross section and the pivot element may include a head portion having the first clamping portion in the form of a part circular bore therethrough for receiving the arm. In the preferred embodiment, the cross section of the bore includes a first circular part having a diameter larger than the diameter of the arm and a second circular part having a diameter closely matching the diameter of the circular rod or arm. The centers of the two circular bore parts may be offset from one another, thus forming a pair of concentric circular areas. At the end of the pivot element opposite the head, the pivot element may be in the form of a threaded rod or screw shank which extends from the head portion along an axis which, upon assembly of the first and second rod gripping elements and the pivot element, is coaxial with the second axis.

In the preferred embodiment, the bore in the head of the pivot element extends along an axis transverse to the axis of the threaded portion of the pivot element and, upon assembly on the arm, is parallel to the first axis. Upon clamping of the assembled cross connector, the arm is moved into the second smaller circular part of the bore so the second circular part and the arm are essentially coaxial.

In the preferred embodiment, there are two bearing surfaces on the second rod connecting element. First is a flat surface area which surrounds the hole through the second end which receives the threaded portion of the pivot element. A second bearing surface is formed on the inner cylindrical surface located within the hole of the second element. This second bearing contacts a cylindrical bearing surface formed around the pivot element intermediate the head and the threaded portion. In the preferred embodiment, the bearing member of the second rod connecting element is in the form of a plate or flange having a hole therethrough for receiving the cylindrical bearing surface of the pivot element with the thickness of the plate determining the length of the cylindrical bearing surface which contacts the cylindrical bearing surface on the pivot element. The surface of the plate facing the head of the pivot element acts as the first bearing surface and engages the arm on the first rod gripping element when the assembly is locked. This is because the bore in the head of the pivot element forming the first clamping portion extends through a portion of the cylindrical bearing surface between the head and the threaded portion with the diameter of the arm dimensional to extend into the cylindrical bearing surface when the arm is fully positioned in the second part of the bore in the head. Thus, the first bearing surface surrounding the hole on the second end of the second rod gripping element engages the outer surface of the arm or rod when the second element is positioned on the threaded portion of the pivot element with the bearing surface in the bore on the second element engaging the cylindrical bearing surface on the pivot element. Consequently, a gap is always left between a surface of the head adjacent the cylindrical bearing surface and the adjacent first bearing surface on the second element.

A lock nut engageable with threaded portion of the pivot element acts against the area of the second element surrounding said bore on the side opposite said first bearing surface and, upon tightening, moves the first bearing surface towards the head of the bearing element and into engagement with the outer surface of the arm. Upon sufficient tightening of the lock nut on the threaded portion of the pivot element, the first bearing surface on the second element forces the arm from the first circular part in the head to the smaller second circular part in the head and causing the frictional engagement between all of the relatively movable parts to lock the assembly together in a fixed position.

Conversely, loosening the locking nut permits adjustment of the length of the device along the first axis and allows rotation of the second axis about the first axis by pivoting the head of the clamping element about the arm and changing the angular relationship between the hooked portions by rotation of the second element about the second axis.

The first rod gripping element, the second rod gripping element, and the clamping element may be held loosely together by a stop on the end of the arm or rod. The stop maybe made by upsetting the material at the end of the arm, thus forming a diameter greater than the larger first diameter of the bore in the head to thereby prevent the head from disengaging from the arm once assembled. The lock nut can be placed loosely on the threaded portion of the pivot element, thereby allowing relative motion but preventing the unintentional disassembly of the cross connector.

The extension arm on the first element may either be integral with the gripping element or maybe pre-assembled thereto in any manner or the arm may have a threaded end threaded into body of the first rod connecting element so that different length arms maybe utilized with the clamping element at the time of surgery.

These and other objects and advantages of the present invention will become apparent from the following description of the accompanying drawings, which disclose several embodiments of the invention. It is to be understood that the drawings are to be used for purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
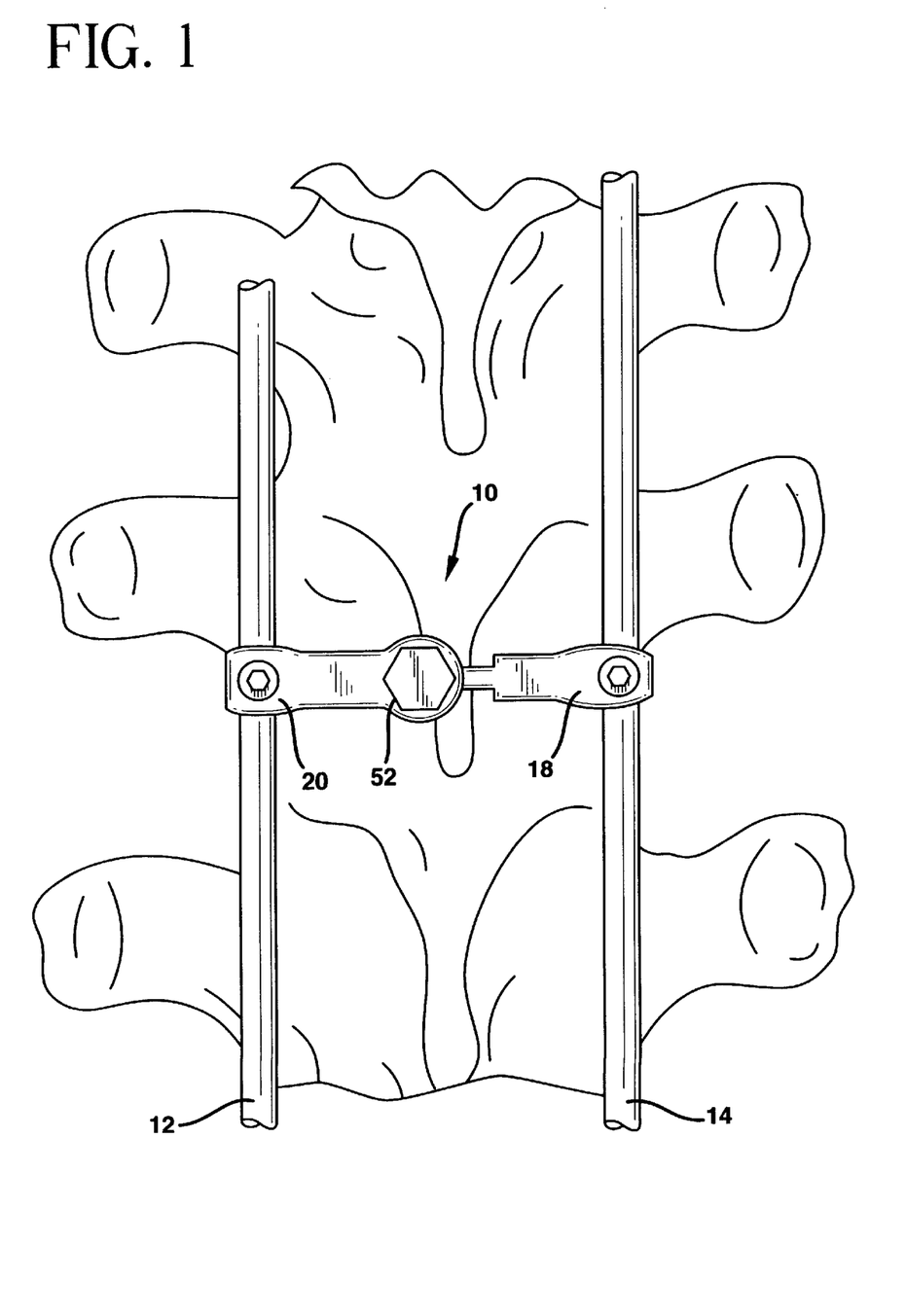
FIG. 1 is an elevation view of the vertical plane of the spine, including the cross connectors of the present invention coupling a pair of stabilizing rods mounted on the vertebra pedicles.

Referring to FIG. 1, there is shown the cross connector assembly of the present invention, generally denoted at 10 connecting a pair of rods, 12 and 14, of a spinal osteosynthesis system. This interconnection is preferably accomplished by sizing the cross connector 10 to extend between rods 12 and 14.

Figure 2:
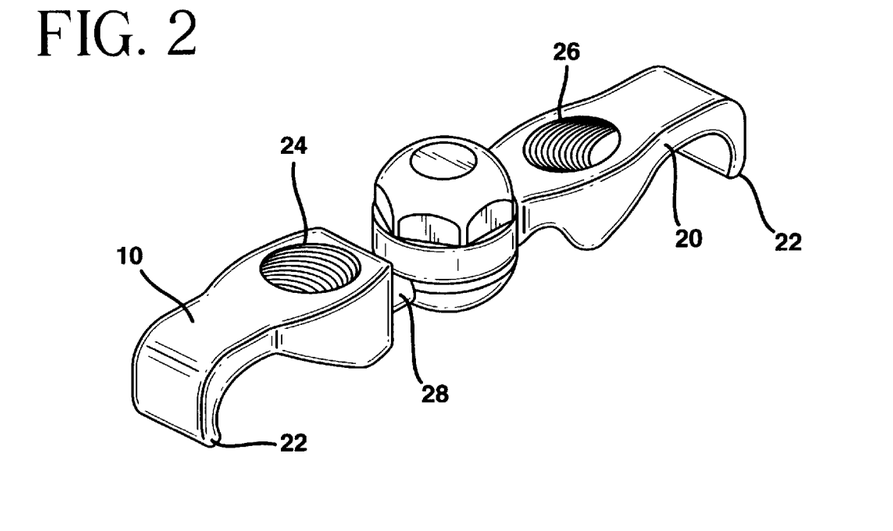
FIG. 2 is an isometric view of one of the cross connector shown in FIG. 1.
Figure 3:
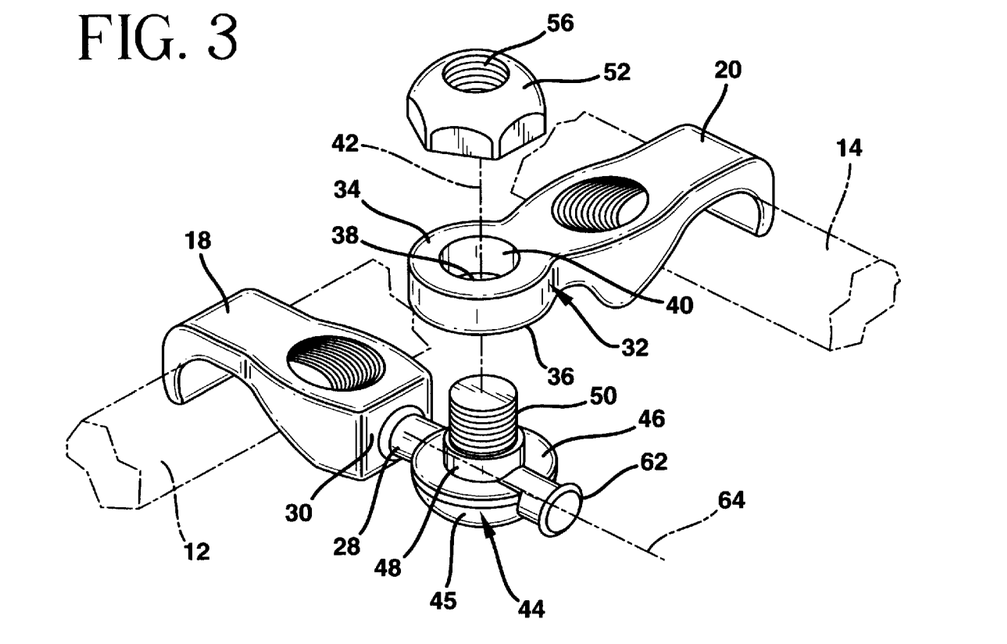
FIG. 3 is an exploded view of the cross connector shown in FIG. 1 mounted on a pair of rods.

Referring to FIGS. 2 and 3, there is shown the cross connector 10 of the present invention, which consists of a first rod gripping element 18 and a second rod gripping element 20. In the preferred embodiment, both rod gripping elements 18 and 20 include bodies with hook portions 22 formed at one end. Also in the preferred embodiment, both rod gripping portions include angled holes 24 and 26 which are threaded to accommodate a set screw (not shown) utilized to lock one of the rods 12, 14 or 16 within the hooked portion 22.

First rod gripping element 18 includes an extension arm 28 which may be in the form of a rod or shaft formed integrally with the connecting element 18, such as by welding or by machining both the gripping element 18 and the arm 28 from a single piece of material. Alternately the end of arm 28 adjacent rod gripping element 18 maybe threaded and screwed into a corresponding threaded bore formed on surface 30 of rod gripping element 18.

Rod gripping element 20 includes a bearing portion 32 formed on an end thereof opposite the end including hook portion 20. The bearing portion includes an upwardly facing surface 34 and a first bearing surface 36 surrounding a bore 38. Bore 38 includes a second bearing surface 40 internal of bore 38 extending parallel to axis 42.

A pivot element generally denoted as 44 includes a head 45 having a surface 46 and a cylindrical bearing surface 48 and a threaded portion 50. Also included is a lock nut 52 with a threaded bore 56.

Figure 4A:
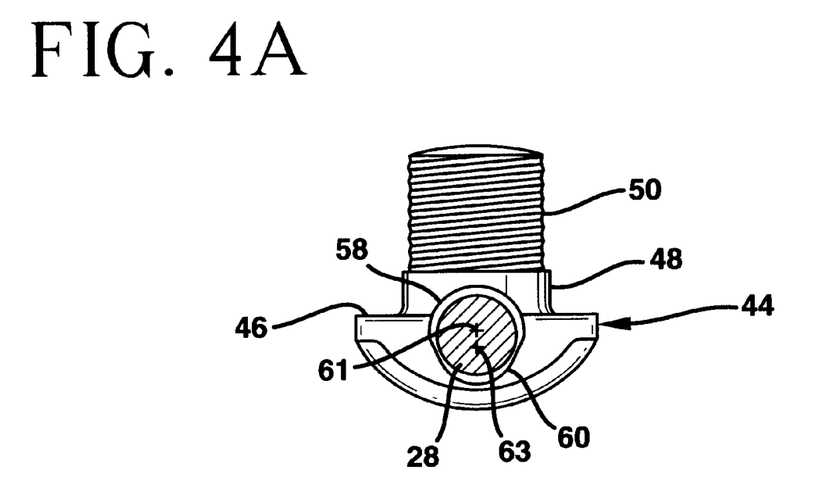
FIG. 4A is an elevation view of the pivot element of the present, with the arm positioned therein.
Figure 4B:
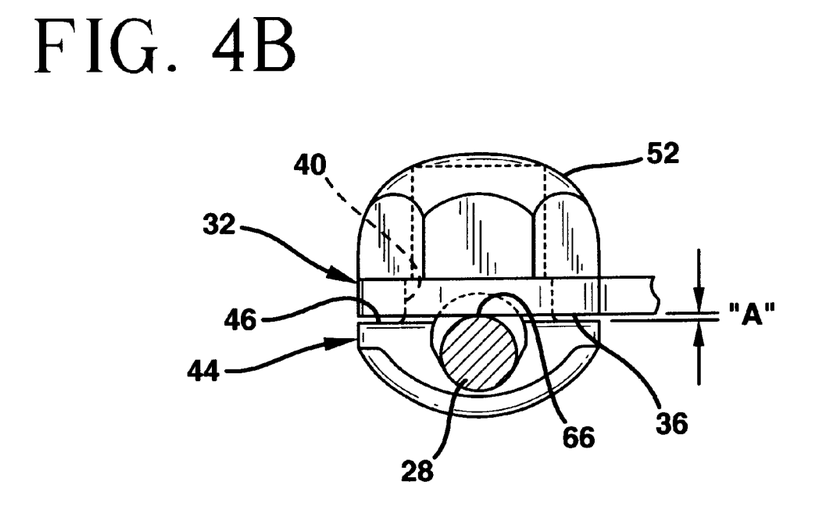
FIG. 4B is an elevation view of the pivot element and pivot arm of FIG. 4A being clamped together by a locking nut.

Referring now to FIGS. 4A and 4B, there is shown an elevation view of pivot element 44 in an unassembled condition in 4A and assembled with lock nut 52 in FIG. 4B. In both views, arm 28 is shown in cross-section. As can be best seen in FIG. 4A, head 45 of pivot element 44 includes a bore composed of two circular sections 58 and 60 having different diameters. The diameter of circular section 60 closely matches that of the side diameter of arm 28 which, in the preferred embodiment, is circular in cross-section. The circular portion 58 has a somewhat larger diameter and, in the preferred embodiment has a center 61 offset from the center 63 of circular portion 60. This results in the bore in head 45 having an eccentric shape.

As can be best seen in FIG. 4B, cylindrical bearing surface 40 of bore 38 is positioned to pivot on bearing surface 48 of pivot element 44 when completely assembled. In addition, the diameter of arm 28 and circular bore portions 58 and 60 and the location of surface 46 are dimensioned such that upon complete assembly a portion of arm 28 always extends beyond surface 46, leaving a gap "A" between surface 46 and surface 36.

Pivot element 44 may be permanently assembled onto arm 28 during manufacture. This permanent mounting is accomplished by placing pivot element 44 on the arm and forming a flange 62 at the free end of arm 28 and then permanently attach the arm to the body of the first gripping element. Flange 62 maybe formed by upsetting the material at the free end of the arm. The diameter of upset portion 62 is larger than the opening in pivot element 44 formed by combined circular bores 58 and 60. Thus, while pivot element 44 is freely slidable on arm 28, it cannot become disengaged. Alternatively, the end of arm 28 may be threaded into a bore in rod gripping element 18 in which case the pivot element is placed on arm 28 prior to being threaded into element 18. The flange 62 will still keep the pivot element 44 from disengaging. This procedure can be done at the time of use.

Figure 5:
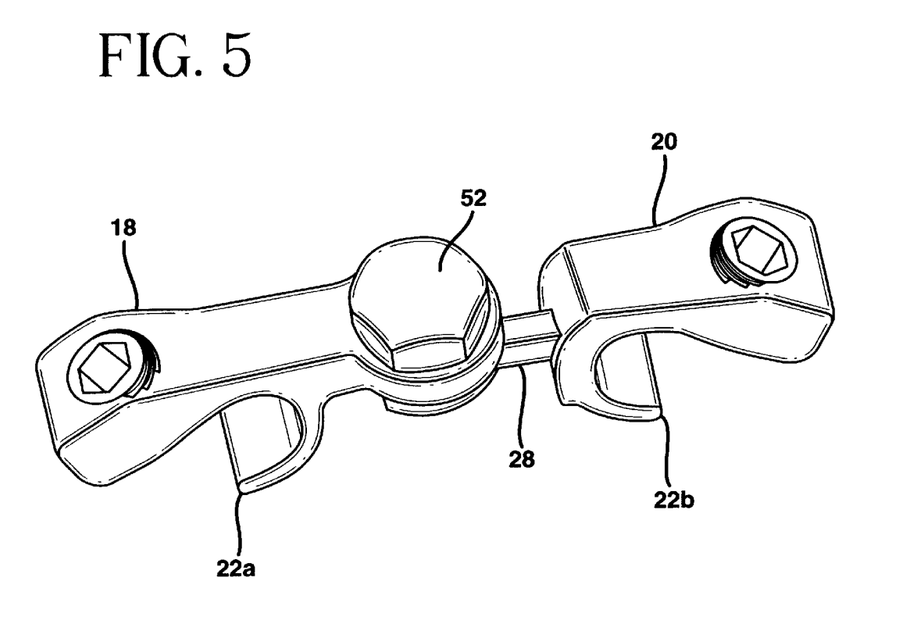
FIG. 5 is an isometric view of the cross connector of the present invention, including two gripping portions facing away from one another.
Figure 5A:
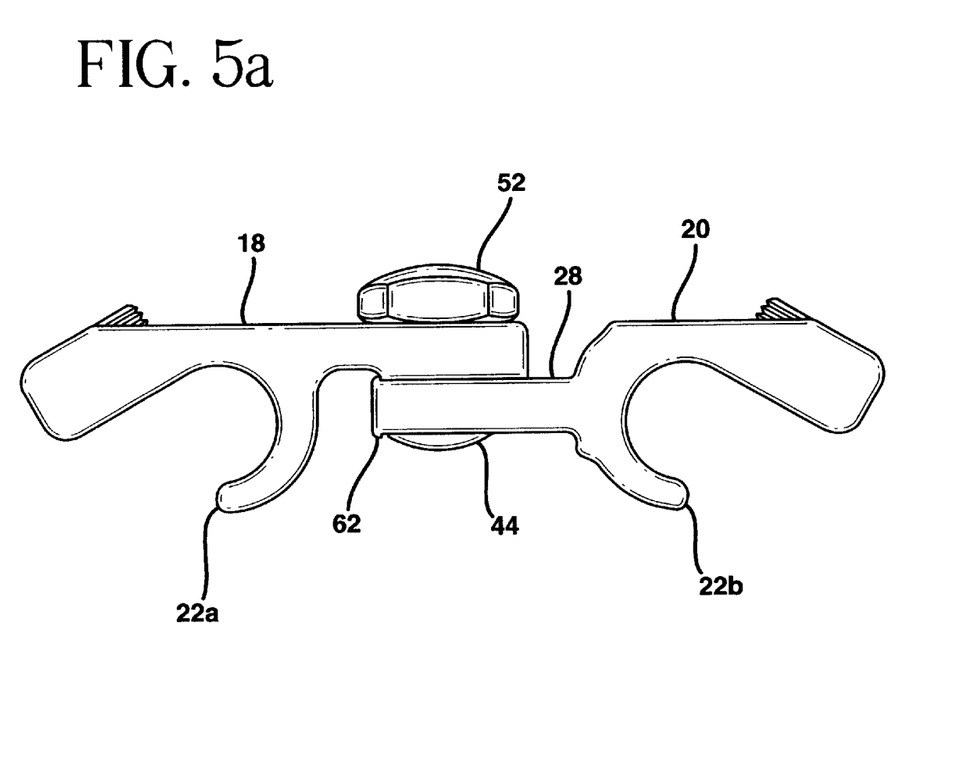
FIG. 5A is an elevation view of the cross connector embodiment shown in FIG. 5.
Figure 6:
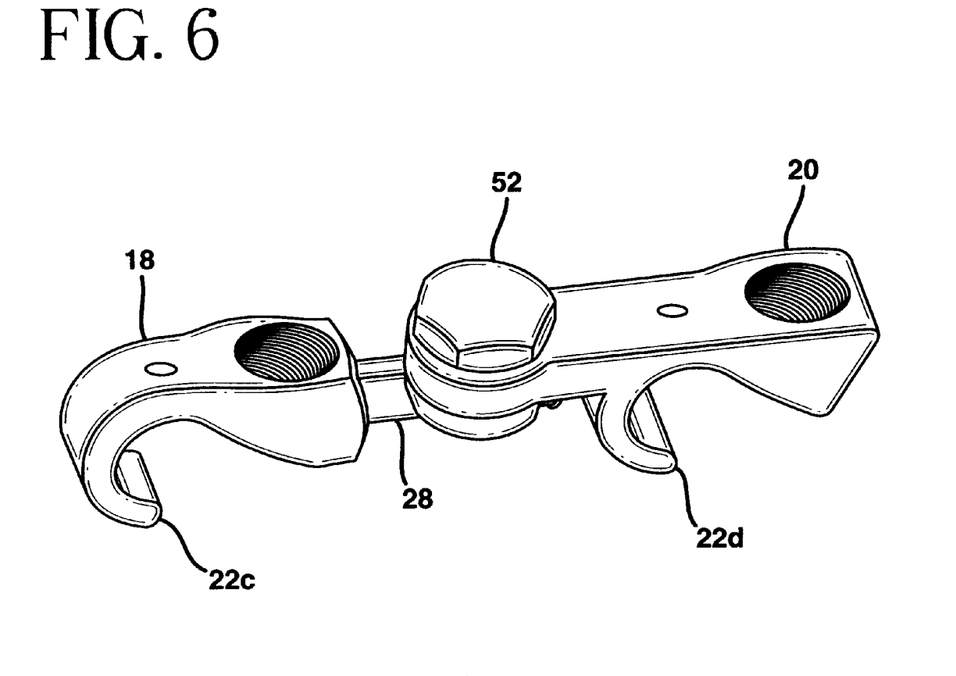
FIG. 6 is an isometric view of the cross connector of the present invention showing gripping portions both facing in the same direction.
Figure 7:
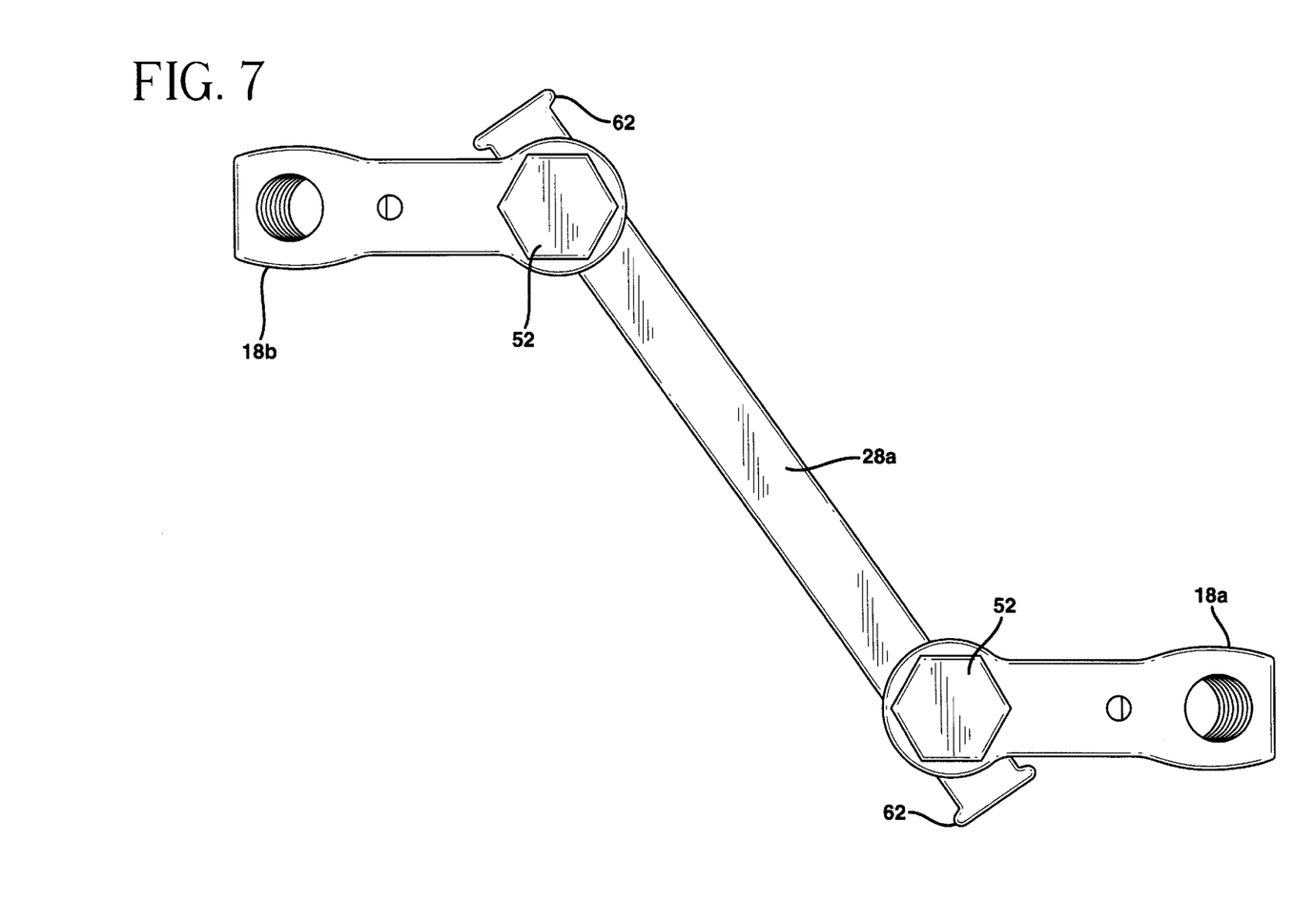
FIG. 7 is a top view of the cross connector of the present invention, including an intermediate rod connecting a pair of pivoted rod gripping portions.

Alternate embodiments are shown in FIGS. 5 through 7. In the embodiment of FIGS. 5 and 5A, the cross connector is the same as that described above, except for the gripping members. In the embodiment of FIG. 5, the rod gripping elements 18 and 20 are in the form of hooks 22a and 22b which face away for each other. Hook portions 22a and 22b face away from each other so that even closely spaced rods 12, 14 can be accommodated by the cross connector 10. By facing the curved portions of the hooks away from each other, the cross connector can fit completely between the rods 12, 14 and grip the rods from the inside. Such a connector is shorter in length than a cross connector with hooks facing towards each other and designed to grip the rods from the outside. The positioning of angled holes 24 and 26 are oriented so that the set screw is directed in the direction of the rod to be gripped.

Figure 6A:
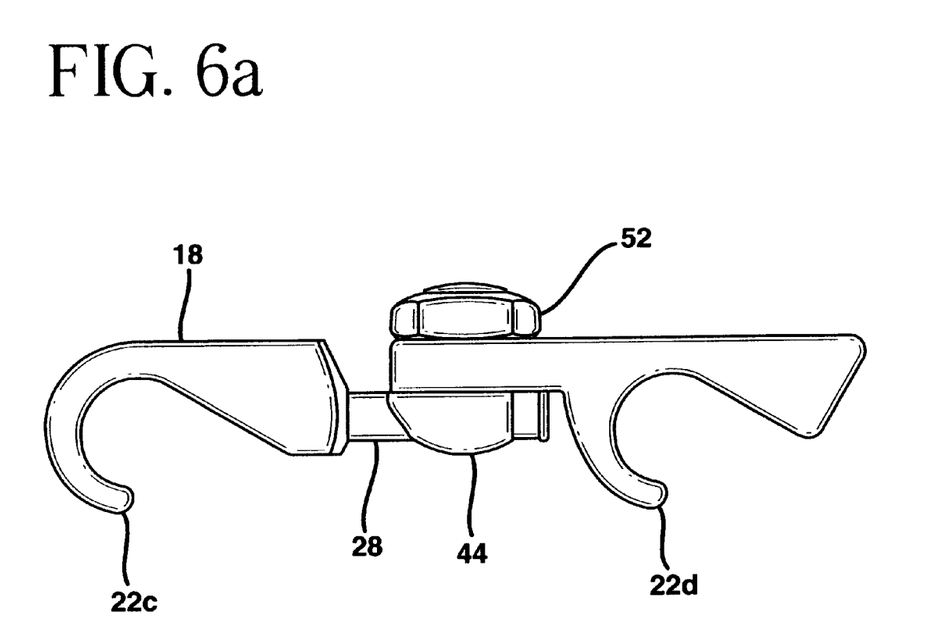
FIG. 6A is an elevation view of the cross connector shown in FIG. 6.

With regard to FIGS. 6 and 6A, a cross connector is shown which includes hook portions 22c and 22d which face in the same direction, thus allowing the cross connector to be slid into position by movement of cross connector 10 and rod gripping elements 18 and 20 in the same direction with respect to the rods 12, 14. Again, one of the holes, 24 or 26 is oppositely oriented so that the set screw properly engages the rod. This design also allows somewhat closer spacing between rods 12, 14 than if the hooks 22 of FIG. 1 which face each other.

Referring to FIG. 7, there is shown two rod gripping elements 18a and 18b similar in design to rod gripping element 18 shown in FIG. 3. However, instead of an arm 28 being fixed to one of the rod gripping elements, an elongated arm 28a is provided which extends between elements 18a and 18b through a pivot element 44 on each of the elements 18a and 18b. Pivot element 44 is identical to that shown in FIGS. 4A and 4B so that elements 18a and 18b may be spaced in the proximal distal direction along rods 12 and 14. Rod 28a includes stop 62 and on each end to prevent disassembly of the structure. In the preferred embodiment, the length of rod 28a may be from 30 to 100 mm and, if necessary, elongated rod 28a may be bent in the posterior direction with the use of a rod bending instrument (not shown) to avoid any bony masses in the spine area. Of course, rod 28a may be bent in other directions, if necessary, to avoid contacting bone. The use of two pivot elements 44 enables rod gripping portions 18a and 18b to be oriented in a multitude of angular orientations.

During assembly, cross connector 10 maybe loosely assembled by placing bore 38 over the threaded portion 50 of the pivot element 44 and partially tightening lock nut 52 on threaded portion 50. The rod gripping elements 18 and 20 may then be positioned in any angular relationship with respect to one another and can also be moved towards or away from one another along axis 64 which extends along arm 28. Once hook portions 22 are placed over and locked onto rods 12, 14 by set screws (not shown), then the cross connector assembly maybe locked in a fixed position.

This is accomplished by tightening lock nut 52 which moves surface 36 of bearing portion 32 towards surface 46 of the pivot element until surface 36 engages the outer curved surface 66 of arm 28. At this point, arm 28 is moved out of circular bore 58 into circular bore 60 and since the parts are dimensioned so that gap "A" is always present, surface 36 forces rod 28 into the tightly conforming bore 60. The dimensions of the outer diameter of rod 28 and the inner surface of bore 60 closely match such that sufficient friction is created to prevent both the rotation of pivot element with respect to arm 28 and the sliding of pivot element 44 with respect to arm 28. Likewise, the pressure of lock nut 52 on surface 34 of bearing portion 32 is sufficient to prevent rotation about axis 42. Thus, the cross connector is locked in position. If the surgeon wishes to rearrange the rod system, he merely loosens nut 52 which then permits rotation about axis 42 and 64, as well as movements along arm 28.

In the preferred embodiment, the diameter of the arm or rod 28 is 3.0+0.00−0.05 mm and the diameter of the circular bore 60 is 3.0+0.05−0.00 mm with the distance from the center of bore 60 to surface 46 being 1.25+0−0.05 mm so that a gap "A" of approximately 0.25 mm is present when the assembly is tightened. The dimension of the length of the arms or rods 28 in the preferred embodiment is 12–42 mm with the upset portion at the end of the arm being 3.4 mm in diameter which is larger than the narrowest portion of the intersecting bores 58 and 60. As indicated above, the arm may be removable in which case the arms of different length are screwed into element 18 or, alternatively, different elements 18 may be provided with permanent arms of different lengths. The head 45 of pivot element may be circular or may be part circular with a flatter portion facing body 22 of element 18 when mounted on arm 28. This allows the pivot element to be mounted closer to element 18 when mounted on arm 28 than would be the case if head 45 were entirely circular.

While there have been described and illustrated cross connector devices for coupling dual rods of orthopaedic apparatus together and providing enhanced stability thereto, it will be apparent to those skilled in the art that variations and modifications are possible without deviating from the broad spirit and principle of the present invention which shall be limited solely by the scope of the claims appended hereto.

What is claimed is:

1. A cross connector for connecting spinal rods, comprising:
    a first element having a rod gripping member formed on a first end thereof and having an arm extending from a second end thereof along a first axis;
    a second element having a rod gripping member formed on a first end thereof and a bearing portion formed on a second end thereof; and
    a pivot element slidably and rotatably coupled to said arm for movement along and rotation about said axis, said pivot element including a bearing surface engageable with a bearing surface on said bearing portion formed on said second element, said bearing surfaces allowing relative rotation between said pivot element and said second element about a second axis which is not parallel to said axis of said arm.

2. The cross connector of claim 1, wherein said rod gripping members are hook shaped.

3. The cross connector of claim 2, wherein each of said hook shaped gripping members has a curved portion.

4. The cross connector of claim 3, wherein said curved portion on said rod gripping members face in the same direction.

5. The cross connector as set forth in claim 1, wherein the arm on said first element is a longitudinally extending shaft of circular cross section and said pivot element has a part circular bore therethrough for receiving said arm.

6. The cross connector as set forth in claim 5, wherein the cross section of said bore includes a first circular part having a diameter larger than the diameter of said arm and a second circular part having a diameter closely matching the diameter of said arm.

7. The cross connector as set forth in claim 6, wherein the centers of said first and second circular parts of said bore are offset from one another.

8. The cross connector as set forth in claim 6, wherein said pivot element includes a head portion containing said bore and a threaded portion extending from said head portion along said second axis.

9. The cross connector as set forth in claim 8, wherein said bore extends along an axis transverse to said second axis.

10. The cross connector as set forth in claim 8, wherein said first and second axes are perpendicular.

11. The cross connector as set forth in claim 8, wherein said bearing surface on said pivot element is cylindrical in form and concentric with the axis of said threaded portion.

12. The cross connector as set forth in claim 11, wherein said cylindrical bearing surface extends between said head portion and said threaded portion of said pivot element.

13. The cross connector as set forth in claim 12, wherein said bearing portion of said second element is in the form of a plate having a bore for receiving the cylindrical bearing surface of said pivot element and includes a planar bearing surface surrounding said bore.

14. The cross connector as set forth in claim 13, wherein said bore in said head extends through a portion of said cylindrical bearing surface.

15. The cross connector as set forth in claim 14, wherein the cross section of said arm extends into said cylindrical bearing surface when said arm is positioned in said second circular part of said bore.

16. The cross connector as set forth in claim 15, wherein said bearing surface on said second element engages said arm when the second element is positioned on said threaded portion with said bore on said second rod gripping element engaging said cylindrical bearing surface on said pivot element to permit relative rotation therebetween.

17. The cross connector as set forth in claim 16, further including a lock nut threaded onto said threaded portion and clamping said planar bearing surface of said second element against said arm and positioning said arm within said second circular part of said bore of said pivot element.

18. The cross connector as set forth in claim 6, wherein said arm has a stop formed on a free end thereof at the second end of said first element, said stop having a cross section larger than the cross section of said first circular part of said bore in said pivot element.

19. The cross connector of claim 18, wherein said arm extends a distance greater than halfway between a pair of spinal rods.

20. A spinal cross connector comprising:
    a first element having a body, a rod gripping portion formed on a first end of said body and a circular rod extending along a first axis from a second end of said body;
    a second element having a body, a rod gripping portion formed on a first end of said body and a flange, including a bore having a bearing portion extending from a second end of said body;
    a pivot element having a head portion, including a bore therethrough for engaging said circular rod, a threaded portion extending from said head portion along a second axis and a generally cylindrical bearing surface engageable with said bearing portion on said flange; and
    a lock nut operatively engageable with said threaded portion on said pivot element.

21. The cross connector of claim 20, wherein said rod gripping portions are hook shaped.

22. The cross connector of claim 21, wherein each of said hook shaped gripping portions has a curved portion.

23. The cross connector of claim 22, wherein said curved portion on said rod gripping portions face in the same direction.

24. The cross connector as set forth in claim 20, wherein a cross section of said bore in said pivot head includes a first circular part having a diameter larger than the diameter of said arm and a second circular part having a diameter closely matching the diameter of said arm.

25. The cross connector as set forth in claim 24, wherein the centers of said first and second circular parts of said bore are offset from one another.

26. The cross connector as set forth in claim 24, wherein said bore extends along an axis transverse to said second axis.

27. The cross connector as set forth in claim 20, wherein said first and second axis are perpendicular.

28. The cross connector as set forth in claim 20, wherein said cylindrical bearing surface extends between said head portion and said threaded portion of said pivot element.

29. The cross connector as set forth in claim 20, wherein said bore in said head portion extends through a portion of said cylindrical bearing surface.

30. The cross connector as set forth in claim 29, wherein a cross section of said rod extends into said cylindrical bearing surface when said rod is positioned in a second circular part of said bore having a diameter closely matching the diameter of said rod.

31. The cross connector as set forth in claim 30, wherein said bearing surface on said second element engages said rod when the second element is positioned on said threaded portion with said bore on said second rod gripping element engaging said cylindrical bearing surface on said pivot element to permit relative rotation therebetween.

32. The cross connector as set forth in claim 31, wherein said lock nut is threaded onto said threaded portion and clamps said planar bearing surface of said second element against said arm and positions said arm within said circular part of said bore of said pivot element.

33. The cross connector as set forth in claim 20, wherein said circular rod has a stop formed on free end thereof at the second end of said first element, said stop having a cross section larger than the cross section of said bore in said pivot element.

34. A cross connector for connecting spinal rods, comprising:
 a first element having a rod gripping member formed on a first end thereof;
 a second element having a rod gripping member formed on a first end thereof and a bearing portion formed on a second end thereof, and
 a pivot element slidably and rotatably to a second end of said first element for movement along and rotation about a first axis, said pivot element including a bearing surface engageable with a bearing surface on said bearing portion formed on said second element, said bearing surfaces allowing relative rotation between said pivot element and said second element about a second axis which is not parallel to said first axis.

35. The cross connector of claim 34, wherein said rod gripping members are hook shaped.

36. The cross connector of claim 35, wherein each of said hook shaped gripping members has a curved portion.

37. The cross connector of claim 36, wherein said curved portion on said first and second rod gripping members face in the same direction.

38. The cross connector as set forth in claim 34, wherein said first element includes an arm in the form of a longitudinally extending shaft of circular cross section and said pivot element has a part circular bore therethrough for receiving said arm.

39. The cross connector as set forth in claim 38, wherein the cross section of said part circular bore includes a first circular part having a diameter larger than the diameter of said arm and a second circular part having a diameter closely matching the diameter of said arm.

40. The cross connector as set forth in claim 39, wherein the centers of said first and second circular parts of said bore are offset from one another.

41. The cross connector as set forth in claim 39, wherein said pivot element includes a head portion containing said bore and a threaded portion extending from said head portion along said second axis.

42. The cross connector as set forth in claim 41, wherein said bearing surface on said pivot part is cylindrical in form and concentric with the axis of said threaded portion.

43. The cross connector as set forth in claim 42, wherein said cylindrical bearing surface extends between said head portion and said threaded portion of said pivot element.

44. The cross connector as set forth in claim 42, wherein said bearing portion of said second element is in the form of a plate having a bore for receiving the cylindrical bearing surface of said pivot element and includes a planar bearing surface surrounding said bore.

45. The cross connector as set forth in claim 42, wherein said bore in said head extends through a portion of said cylindrical bearing surface.

46. The cross connector as set forth in claim 45, wherein the cross section of said arm extends into said cylindrical bearing surface when said arm is positioned in said second circular part of said bore.

47. The cross connector as set forth in claim 46, wherein said bearing surface on said second element engages said arm when the second element is position on said threaded portion with said bore on said second rod gripping element engaging said cylindrical bearing surface on said pivot element to permit relative rotation therebetween.

48. The cross connector as set forth in claim 47, further including a lock nut threaded onto said threaded portion and clamping said planar bearing surface of said second element against said arm when said arm is within said second circular part of said bore of said pivot element.

* * * * *